United States Patent [19]

Saita et al.

[11] Patent Number: 5,128,169
[45] Date of Patent: Jul. 7, 1992

[54] METHOD FOR FORMING HYDROXYAPATITE COATING FILM

[75] Inventors: Kenji Saita; Shinji Fujiwara, both of Tsukuba, Japan

[73] Assignee: Sumitomo Chemical Company, Limited, Osaka, Japan

[21] Appl. No.: 636,579

[22] Filed: Jan. 2, 1991

[30] Foreign Application Priority Data

Jan. 8, 1990 [JP] Japan .................................. 2-2299

[51] Int. Cl.$^5$ .............................................. A61K 6/00
[52] U.S. Cl. ................................ 427/2; 623/16; 423/309; 423/311
[58] Field of Search ............... 427/2; 623/16; 423/309, 423/311

[56] References Cited

U.S. PATENT DOCUMENTS

| Re. 33,161 | 2/1990 | Brown et al. | 623/16 |
| 3,387,925 | 6/1968 | Vanstrom et al. | 423/311 |
| 4,097,935 | 7/1978 | Jarcho | 423/307 |
| 4,623,553 | 11/1986 | Ries et al. | 427/2 |
| 4,699,742 | 10/1987 | Nakamura et al. | 264/56 |
| 4,911,953 | 3/1990 | Hosonuma et al. | 427/2 |
| 4,917,702 | 4/1990 | Scheicher et al. | 623/16 |
| 4,983,182 | 1/1991 | Kijima et al. | 427/2 |
| 4,988,362 | 1/1991 | Toriyama et al. | 427/2 |
| 5,030,474 | 7/1991 | Saita et al. | 427/2 |
| 5,068,122 | 11/1991 | Kokubo et al. | 427/2 |

FOREIGN PATENT DOCUMENTS 0322250 12/1988 European Pat. Off. .
3709457 10/1987 Fed. Rep. of Germany .
53-118411 10/1978 Japan .

*Primary Examiner*—Michael Lusignan
*Assistant Examiner*—Diana L. Dudash
*Attorney, Agent, or Firm*—Birch, Stewart, Kolasch & Birch

[57] ABSTRACT

A method for forming a hydroxyapatite coating film on a substrate which comprises coating a dispersion of flocculated colloids of hydroxyapatite on a substrate and drying. The coating method of this invention does not require heating of the coated substrate to high temperature and hence can also be applied to a substrate which is easily deteriorated with heat. The coated substrate of this invention has excellent strength and adhesion force and is useful in a variety of fields, particularly as an implant and as a material, adsorbing and separating agent.

19 Claims, No Drawings

METHOD FOR FORMING HYDROXYAPATITE COATING FILM

TECHNICAL FIELD

This invention relates to a method for forming a hydroxyapatite coating film on a surface of a substrate, which product is useful as an implant material in view of its excellent affinity to a living body.

TECHNICAL BACKGROUND AND PRIOR ART

Calcium phosphate, especially hydroxyapatite, has excellent affinity to the living body and an excellent adsorptivity and hence has been studied as to the utilities thereof in a variety of fields, particularly use thereof as implant material for replacing or repairing hard tissues of living bodies. The implant material is required to have biodynamic strength in addition to an affinity to living body. Nevertheless, hydroxyapatite is not satisfactory in terms of the strength even in the form of a sintered product. Accordingly, from a practical viewpoint, it is favorable to use a substrate or core material such as metallic materials, ceramics, glass, etc. and to form a hydroxyapatite coating film on the surface of said substrate or core material.

Various methods have hitherto been proposed for forming a coating film of calcium phosphate. For example, a thermal plasma spray method (cf. Japanese Patent First Publication (Kokai) No. 82893/1977), a spattering method (cf. Japanese Patent First Publication (Kokai) No. 109049/1983), a physical vapor deposition (PVD) or chemical vapor deposition (CVD) method (cf. Japanese Patent First Publication (Kokai) No. 111753/1984), an electrophoretic method (cf. Japanese Patent First Publication (Kokai) No. 128190/1978), and a coating method (cf. Japanese Patent First Publication (Kokai) No. 118411/1978) has been proposed.

However, the thermal plasma spray method, spattering method, CVD method and PVD method are with difficulty applied to a substrate having a complicated shape, for example, onto the inner surface of porous substrate electrophoretic method can not be used to form the coating film onto a substrate having no electrical conductivity. On the other hand, the coating method is advantageously easy in the treatment, and the above-mentioned Japanese Patent First Publication (Kokai) No. 118411/1978 discloses a method for forming a coating film by suspending fine particles of apatite in water and coating the aqueous suspension onto the surface of a substrate, followed by calcining the coated substrate. However, this coating method still exhibits a problem in that it is usually difficult to prepare very fine particles of apatite and the particles are easily agglomerated, and further, the particles dispersed in water have usually a particle size of more than 0.5 μm, and hence, the apatite has less adhesiveness with respect to the substrate surface and the coating film is easily peeled off from the substrate. The coating method may also be carried out by coating a suspension of fine particles of apatite in the presence of a water soluble high molecular substance on a surface of a substrate, followed by calcining the coated substrate, thereby burning off the high molecular substance. According to this method, the adhesiveness is improved, but it can not be applied to a material such as titanium which is denatured at a calcining temperature.

SUMMARY DESCRIPTION OF THE INVENTION

Under the above circumstances, the present inventors have intensively studied conventional problems to develop an improved method for forming a hydroxyapatite coating film onto a substrate by a coating method by using a coating liquor containing no organic material which requires calcining at a high temperature for the purpose of forming a coating film having excellent adhesiveness without a calcining step and further taking into consideration that it is important to retain the fine particles of hydroxyapatite in the coating liquor. As a result, it has been found that the desired hydroxyapatite coating film having good properties can be formed by using a specific coating liquor comprising a dispersion of flocculated colloids of hydroxyapatite having a specific sedimentation volume.

An object of the invention is to provide a method for forming a hydroxyapatite coating film by coating a dispersion of flocculated colloids of hydroxyapatite having a sedimentation volume of more than 27 ml/g onto a surface of a substrate, followed by drying the resulting coated substrate. Another object of the invention is to provide an improved method for forming a hydroxyapatite coating film having excellent adhesiveness and excellent strength onto the surface of a substrate to give a product particularly useful as an implant material. These and other objects and advantages of the invention will be apparent to those skilled in the art from the following description.

DETAILED DESCRIPTION OF THE INVENTION

The hydroxyapatite used in this invention is not specified but may be any conventional product which can be prepared by a conventional method, such as wet process or dry process, among which the wet process is preferable because a product having fine particle size can easily be obtained. Particularly, the product prepared by a wet process is more preferably used without drying after filtering and washing with water because undesirable production of agglomerates is inhibited. However, if it is to be dried, it is preferably dried by lyophilization.

As to the particle size of hydroxyapatite, it is reported that a hydroxyapatite prepared by wet process usually has a particle size of about 0.03 μm, but it has a particle size of 0.1 to 1 μm when measured by a sedimentation method even when it is sufficiently dispersed. In said measurement, the particle size is measured as to the primary flocculated particles. The primary flocculated particles can maintain the dispersion state at a high surface charge, but they secondarily flocculate at a low surface charge to induce sedimentation. When the particles form a larger flocculate, they have larger sedimentation speed and larger sedimentation volume.

The dispersion of flocculated colloids of hydroxyapatite used in the method of this invention is prepared in the following manner.

The hydroxyapatite used in this invention is prepared by a conventional wet process, i.e. by mixing an aqueous solution of a calcium salt and an aqueous solution of a phosphate at a neutral or alkaline region. The calcium salt includes calcium chloride, calcium nitrate, calcium acetate, calcium hydroxide, and the like, and the phosphate includes potassium phosphate, sodium phosphate, ammonium phosphate, and the like. The calcium salt is preferably used in a concentration of 0.0005 to 0.6M, more preferably 0.003 to 0.06M. When the concentration of calcium salt is lower than 0.0005M, it becomes lower than the solubility equilibrium of hydroxyapatite and hence the hydroxyapatite is not precipitated. Thus, such a lower concentration is excluded from the desired scope. On the other hand, when the concentration is larger than 0.6M, it tends disadvantageously to form coarse particles of hydroxyapatite. The phosphate is preferably used in a concentration of from 0.0003 to 0.4M, more preferably 0.002 to 0.04M. When the concentration of phosphate is lower than 0.0003M, it becomes lower than the solubility equilibrium of hydroxyapatite and hence the hydroxyapatite is not formed as sediment. Thus, such a lower concentration is excluded from the desired scope. On the other hand, when the concentration is larger than 0.4M, it tends disadvantageously to form coarse particles of hydroxyapatite. The mixing ratio of the calcium salt and the phosphate is preferably in a ratio of Ca/P=1.5-2.0 (atomic ratio), more preferably 1.6-1.7. The mixing is preferably carried out at pH 6-13, more preferably at pH 7-12. When the mixing is carried out at lower than pH 6, there is disadvantageously produced dicalcium phosphate or octacalcium phosphate, and on the other hand, when it is carried out at higher than pH 13, calcium hydroxide is disadvantageously formed as sediment. By mixing the calcium salt and phosphate, white sediment is produced. When the mixture is treated at a temperature of from room temperature to a boiling temperature of the mixture for several hours to several weeks, the ratio of Ca/P in the sediment becomes close to the stoichiometrical ratio of hydroxyapatite, i.e. Ca/P=1.67. The preferred temperature for the treatment is in the range of 60° to 100° C., more preferably 80° to 100° C.

The dispersion state of the produced sediment varies depending on the pH value. At higher than pH 10, the surface charge of the particles becomes larger and hence the particles are easily dispersed, but at lower than pH 10, the particles are easily flocculated. Accordingly, it is preferable to adjust at around pH 7 so that the flocculation is promoted. The flocculate thus formed is formed as sediment by allowing to stand or by centrifugation to produce the desired flocculated colloids.

Alternatively, when powdery hydroxyapatite prepared previously is used, it is dispersed in water (pH 11-13) and the mixture is sufficiently stirred, if necessary it is further subjected to treatment with ultrasonic waves to obtain an aqueous dispersion of hydroxyapatite. By allowing to stand or centrifuging the dispersion, particles having a particle size of more than about 1 μm are formed as sediment. The liquor after removing the thus produced sediment is adjusted to about pH 7 with an acid, and thereby the particles are flocculated and formed as sediment, and the sediment is washed with water and subjected again to sedimentation treatment to produce the desired flocculated colloids.

The dispersion of flocculated colloids used in the present invention is prepared by removing the supernatant liquor from the above mixture containing the flocculated colloids and optionally stirring the resulting mixture. The dispersion of flocculated colloids of hydroxyapatite has a sedimentation volume of more than 27 ml/g, wherein the sedimentation volume means a value obtained by calculating the volume of the flocculated colloids per unit weight of the sediment. When the sedimentation volume is larger, the sediment has larger volume and has preferably larger ability for forming network a in the liquor. However, when the sedimentation volume becomes too larger, the dispersion has a lower concentration of the solid component, which is rather unfavorable as a coating liquor. Thus, the dispersion of flocculated colloids of hydroxyapatite used in this invention has preferably a sedimentation volume of 40 to 150 ml/g.

By using the dispersion of flocculated colloids as prepared above as a coating liquor, the desired coating film is formed on a substrate by applying a stirred dispersion of flocculated colloids to a surface of the substrate, followed by drying the coated substrate. The application of the coating liquor is carried out by conventional methods, such as coating, spraying, dipping, and the like.

The substrate used in this invention includes metallic substrates, ceramics, glass, and the like. However, when the substrate is a hydrophobic substance such as plastics, the coating is hardly applicable, and hence, it is preferable to subject the hydrophobic substance to surface treatment so as to make the surface hydrophilic.

The method of this invention can also be applied to a substrate having complicated shape of surface, for example, to implants having porous surface, such as implants made from metals (e.g. titanium alloy), ceramics (e.g. alumina ceramics), glass materials (e.g. bioglass material).

The substrate coated with the dispersion of flocculated colloids is dried. The drying can be done by any conventional drying method, such as spontaneous drying, hot air drying, and the like, at any temperature, but it is usually dried at lower than 40° C. until the water is distilled off and thereafter it is further well dried at 100° C. or higher. The upper limit of the drying temperature is a temperature at which the substrate is not deteriorated by heating. The preferred drying temperature is in the range of 150° to 200° C.

According to this invention, the hydroxyapatite coating film can be formed with strong adhesiveness and since it does not require being subjected to calcining step. It can also be applied to a substrate which may be deteriorated at a high temperature.

The coated substrate prepared by this invention can be used in a variety of utilities, particularly as an implant material, adsorbing and separating agent, and the like.

EXAMPLES

This invention is illustrated by the following Examples and Reference Examples but should not be construed to be limited thereto. In these examples, % means % by weight unless specified otherwise.

EXAMPLE 1

To a 0.005M aqueous calcium chloride solution (pH 11.6, 100 ml) was added dropwise a 0.003M aqueous potassium dihydrogen phosphate solution (pH 11.6, 100 ml), and the mixture was boiled for one hour and thereafter allowed to stand for 5 days to give flocculated colloids. The mixture was washed by decantation twice, and allowed to stand at room temperature for 2 day, and the supernatant liquor was removed. The dispersion of flocculated colloids thus obtained was well stirred, and a part thereof (0.51 g) was dropped onto a glass plate (25×75×1 mm) The glass plate was air-dried at room temperature for 16 hours and heated stepwise at 90° C., 105° C. and 150° C. for each 20 minutes in a drier. As a result, a uniform coating film was formed on the glass plate.

The coated glass plate was dipped in a mixture of a 0.0005M aqueous calcium chloride solution (100 ml) and a 0.0003M aqueous potassium dihydrogen phosphate solution (100 ml) for 3 days, and thereafter, it was taken out, washed with water and air-dried for one day. As a result, no change of appearance thereof was observed.

The coating film on the substrate was subjected to an adhesion test (by the method described in JIS K5400, K5980), that is, the coating film was cross-cut with a cutter knife with two lines each in longitudinal and transversal directions at intervals of each 5 mm, and thereon a cellophane tape was adhered, and then, the rape was rapidly peeled off. As a result, no peeling of the coating film was observed.

Besides, a part of the dispersion of flocculated colloids obtained above was dried at 150° C., and the solid content was measured. As a result, the dispersion had a concentration of solid component of 1.01 % by weight. Another part of the dispersion of flocculated colloids was added to a 10 ml graduated test tube and the sedimentation volume was measured. As a result, it had a sedimentation volume of 100.1 ml/g.

EXAMPLE 2

In the same manner as described in Example 1 except that a 0.020M aqueous calcium chloride solution (pH 11.6, 100 ml) and a 0.012M aqueous potassium dihydrogen phosphate solution (pH 11.6, 100 ml) g) were used, there was prepared a dispersion of flocculated colloids having a concentration of solid component of 1.29 % by weight and a sedimentation volume of 78.5 ml/g. When the properties of the coating film formed on a glass plate was tested likewise, it showed good properties.

EXAMPLE 3

In the same manner as described in Example 1 except that a 0.040M aqueous calcium chloride solution (pH 11.6, 100 ml) and a 0.024M aqueous potassium dihydrogen phosphate solution (pH 11.6, 100 ml) g) were used, there was prepared a dispersion of flocculated colloids having a concentration of solid component of 1.97 % by weight and a sedimentation volume of 51.0 ml/g. When the properties of the coating film formed on a glass plate was tested likewise, it showed good properties.

EXAMPLE 4

A part of the dispersion of flocculated colloids obtained in Example 1 was dropped onto a titanium plate (10×50×1 mm), and the plate was subjected to drying treatment and dipping treatment in the same manner as in Example 1, and the resultant was subjected to an adhesion test likewise. As a result, no peeling of the coating film was observed.

EXAMPLE 5

To a 0.555M aqueous calcium nitrate solution (pH 10, 0.6 liter) was added dropwise a 0.167M aqueous secondary ammonium phosphate solution (pH 10, 1.2 liter), and the mixture was boiled for one hour and filtered. The precipitates were lyophilized to obtain powdery hydroxyapatite. The powder thus obtained (0.6 g) was added to water (150 ml) and adjusted to pH 11.55 with sodium hydroxide and the mixture was treated with ultrasonic for one minute and stirred with a stirrer for one hour. After allowing to stand for 2.5 hours, the liquor in 40 mm depth from the liquid surface was taken and adjusted to pH 7.4 with nitric acid and washed by decantation three times and then allowed to stand for one day to give flocculate. The supernatant liquor was removed to give a dispersion of flocculated colloids having a concentration of solid component of 0.89 % by weight and a sedimentation volume of 112.3 ml/g. When a part of the dispersion of flocculated colloids was dropped onto a glass plate and subjected to drying in the same manner as in Example 1 and the properties of the coating film formed on a glass plate was tested likewise, it showed good properties.

REFERENCE EXAMPLE 1

In the same manner as described in Example 1 except that a 0.400M aqueous calcium chloride solution (pH 11.6, 100 ml) and a 0.240M aqueous potassium dihydrogen phosphate solution (pH 11.6, 100 ml) were used, there was prepared a dispersion of flocculated colloids having a concentration of solid component of 5.08 % by weight and a sedimentation volume of 18.9 ml/g. When the properties of the coating film formed on a glass plate was tested likewise, it showed many cracks.

REFERENCE EXAMPLE 2

In the same manner as in Example 5 there was obtained powdery hydroxyapatite. The powder thus obtained (0.6 g) was added to water (150 ml) and adjusted to pH 11.2 with sodium hydroxide and the mixture was treated with ultrasonic for one minute and stirred with a stirrer for one hour. After allowing to stand for 15 minutes, the liquor in 45 mm depth from the liquid surface was removed. To the resulting mixture was added water so as to be totally 150 ml, and the mixture was adjusted to pH 11.2 with sodium hydroxide and treated with ultrasonic for one minute and stirred with a stirrer for one hour. After allowing to stand for 4 minutes, the liquor in 40 mm depth from the liquid surface was taken and adjusted to pH 7.0 with nitric acid and washed by decantation three times and then allowed to stand for 5 days to give flocculate. The supernatant liquor was removed to give a dispersion of flocculated colloids having a concentration of solid component of 3.71 % by weight and a sedimentation volume of 25.5 ml/g. When a part of the dispersion of flocculated colloids was dropped onto a glass plate and subjected to drying in the same manner as in Example 1 and the properties of the coating film formed on a glass plate was tested likewise, it showed many cracks.

What is claimed is:

1. A method for forming a hydroxyapatite coating film on a substrate, which comprises coating a dispersion of flocculated colloids of hydroxyapatite having a sedimentation volume of more than 27 ml/g onto a substrate, and drying the coated substrate, wherein the dispersion is prepared by forming sediment of flocculated colloids of hydroxyapatite in a supernatent liquor, removing said supernatant liquor, and, without drying, dispersing the sediment.

2. The method according to claim 1, wherein the flocculated colloids of hydroxyapatite are prepared by mixing an aqueous solution of a calcium salt at a concentration of 0.0005 to 0.6M, and an aqueous solution of a phosphate at a concentration of 0.0003 to 0.4M.

3. The method according to claim 2, wherein the calcium salt and the phosphate are mixed in an atomic ratio of Ca/P equal to 1.5 to 2.0.

4. The method according to claim 2, wherein the mixing of the calcium and phosphate salts is carried out at a pH of 6 to 13.

5. The method according to claim 1, wherein the dispersion of flocculated colloids has a sedimentation volume of 40 to 150 ml/g.

6. The method according to claim 1, wherein the coated substrate is dried at a temperature of 150° to 200° C.

7. The method according to claim 1, wherein the sediment of flocculated colloids of hydroxyapatite in a supernatant liquor is formed by mixing an aqueous solution of a calcium salt and an aqueous solution of a phosphate.

8. The method according to claim 1, wherein the hydroxyapatite has a particle size of 0.1 to 1 microns when measured by a sedimentation method.

9. The method according to claim 1, wherein the calcium salt is a chloride, nitrate, acetate or hydroxide salt.

10. The method according to claim 2, wherein the phosphate salt is a potassium, sodium or ammonium salt.

11. The method according to claim 2, wherein the calcium salt concentration is 0.003 to 0.06M.

12. The method according to claim 2, wherein the phosphate salt concentration is 0.002 to 0.04M.

13. The method according to claim 2, wherein the calcium salt and the phosphate salt are mixed in an atomic ratio of Ca/P equal to 1.6 to 1.7.

14. The method according to claim 2, wherein the mixing of the calcium and phosphate salts is carried out at a pH of 7 to 12.

15. The method according to claim 2, wherein the mixture of calcium and phosphate salts is treated by heating at a temperature in the range of 60° to 100° C.

16. The method according to claim 2, wherein the mixture of calcium and phosphate salts is treated by heating at a temperature in the range of 80° to 100° C.

17. The method according to claim 2, wherein the substrate has a surface which is hydrophilic.

18. The method according to claim 2, wherein the substrate is metallic, ceramic or glass.

19. A method for forming a hydroxyapatite coating on a substrate, which comprises:

preparing a dispersion by mixing an aqueous solution of a calcium salt at a concentration of 0.0005 to 0.6M with an aqueous solution of a phosphate at a concentration of 0.0003 to 0.4M at a pH of 6 to 13 so as to cause sedimentation of flocculated colloids of hydroxyapatite in a supernatant liquor, removing said supernatant liquor, and, without drying, dispersing the sediment so as to form a dispersion of flocculated colloids of hydroxyapatite having a sedimentation volume of more than 27 ml/g;

coating said dispersion on a substrate to form a coated substrate; and drying said coated substrate.

* * * * *